United States Patent
Kawasaki et al.

(10) Patent No.: US 7,725,145 B2
(45) Date of Patent: May 25, 2010

(54) BIOLOGICAL PHOTOMETRIC DEVICE

(75) Inventors: Shingo Kawasaki, Tokyo (JP); Naoki Tanaka, Saitama (JP)

(73) Assignee: Hitachi Medical Corporation, Tokyo (JP)

( * ) Notice: Subject to any disclaimer, the term of this patent is extended or adjusted under 35 U.S.C. 154(b) by 228 days.

(21) Appl. No.: 11/816,452

(22) PCT Filed: Feb. 2, 2006

(86) PCT No.: PCT/JP2006/301720

§ 371 (c)(1),
(2), (4) Date: Aug. 16, 2007

(87) PCT Pub. No.: WO2006/087915

PCT Pub. Date: Aug. 24, 2006

(65) Prior Publication Data

US 2009/0054885 A1  Feb. 26, 2009

(30) Foreign Application Priority Data

Feb. 16, 2005  (JP) ............................. 2005-039450

(51) Int. Cl.
*A61B 5/1455* (2006.01)
(52) U.S. Cl. ...................... 600/328; 600/336
(58) Field of Classification Search .................. 600/322, 600/323, 328, 336; 702/189, 191, 195
See application file for complete search history.

(56) References Cited

U.S. PATENT DOCUMENTS

2003/0060692 A1* 3/2003 L. Ruchti et al. ............ 600/310
2004/0171919 A1* 9/2004 Maki et al. .................. 600/310
2004/0242979 A1  12/2004 Kawasaki
2005/0177033 A1* 8/2005 Kawasaki .................... 600/315

FOREIGN PATENT DOCUMENTS

| EP | 1 685 801 A | 8/2006 |
|---|---|---|
| JP | 03-068336 | 3/1991 |
| JP | 08-215179 | 8/1996 |
| JP | 2000-237194 | 9/2000 |
| JP | 2002-323445 | 11/2002 |
| JP | 2003-010188 | 1/2003 |
| JP | 2004-008504 | 1/2004 |
| JP | 2005-013464 | 1/2005 |
| WO | WO 03/002004 A1 | 1/2003 |
| WO | WO 2004/021889 A1 | 3/2004 |

* cited by examiner

*Primary Examiner*—Eric F Winakur
*Assistant Examiner*—Etsub D Berhanu
(74) *Attorney, Agent, or Firm*—Antonelli, Terry, Stout & Kraus, LLP.

(57) ABSTRACT

A biological photometric device includes a light irradiating unit for irradiating an object to be examined with light having a predetermined wavelength and sympathizing with oxygenated hemoglobin and deoxygenated hemoglobin through an optical fiber, a light detecting unit for detecting and amplifying light passing through a detecting optical fiber and the object as detected signals, a signal processing unit adapted for computing hemoglobin time change information based on oxygenated hemoglobin, deoxygenated hemoglobin and total hemoglobin in the object from the detected signals light detecting unit, and including a noise detector for arithmetically processing the detected signals and determining/detecting whether the time change information is noise attributed to the presence of obstacles to passing of light between the object and the end face of the optical fiber or noise attributed to the damage to the light irradiating unit, and a display unit for displaying the noise signals.

20 Claims, 12 Drawing Sheets

BIOLOGICAL PHOTOMETRIC DEVICE

TECHNICAL FIELD

The present invention relates to a biological photometric device for measuring information in a living body by irradiating light to the inside of the living body and receiving the light reflected or scattered in the living body.

TECHNICAL BACKGROUND

A biological photometric device is capable of measuring blood circulation, hemodynamics or variation of hemoglobin quantity in a living body in a simple manner without much restriction or any harm to the body, by irradiating light within the range from a visible light to infrared light to the living body of an object to be examined, and detecting the reflected light and scattered light passed inside of the living body.

The biological photometric device is used, for example, when a head region is the subject for measurement, for identifying activated state of the brain due to hemoglobin alteration in blood inflowing in a blood vessel in the brain upon physiological stimulation being imparted, or local focus of epileptic seizure, etc.

In Non-patent Document 1, measurement of hemoglobin alteration in a brain upon performing motion/language task, by cerebral blood flow mapping method using near infrared ray is reported. According to the report, it is disclosed that hemoglobin increment in the brain acquired by physiological stimulation such as motion/language task performance is only 5% at the most. This is also confirmed by other measurement methods such as PET (Positron-Emission Tomography).

While variation of hemoglobin amount in the brain due to physiological stimulation amounts to 5% at the most, noise signals measured by a biological photometric device often turn out to be a considerably large value of more than 50% when they are converted into the amount of hemoglobin variation in the brain. Hardly any signals indicating the amount variation of blood accompanying brain function activities are included in these noise signals, and they become a major diagnostic impediment.

In Patent Document 1, a method is described for detecting and eliminating spiky noise signals attributed to gaps generated in the very short period of time between an object and an aperture of optical fibers (hereinafter referred to as spike noise signals) by factors such as displacement of the applied light irradiating unit and light detecting unit. Discrimination between spike noise signals and normal signals is performed by determining whether derivative value of signal intensity is more than a predetermined threshold value or not.

Patent Document 1: WO 03/002004

Non-Patent Document 1: CLINICAL NEUROSCIENCE Vol. 17, No. 11, 1999-11

DISCLOSURE OF THE INVENTION

Problems to be Solved

As mentioned above, it is extremely important in performing clinical diagnosis to detect noise signals that are mixed in hemoglobin alternation signals. While the spike noise detecting method in the above-described Patent Document 1 is capable of detecting precipitous spike noise generated due to gaps generated in the extremely short time between a body surface of an object and an aperture of optical fibers caused by the movement of the object during the examination or by contingent weight added to optical fibers, there are other kinds of noise such as low S/N noise or mirror noise other than spike noise. The spike noise detecting method described in Patent Document 1 is not capable of detecting the low S/N noise or mirror noise.

The objective of the present invention is to provide a biological photometric device capable of discriminating the low S/N noise or mirror noise.

Means to Solve the Problem

In order to achieve the above-mentioned objective, a biological photometric device of the present invention is configured comprising:

a light irradiating unit for irradiating light having predetermined wavelength and sympathizing with oxygenated hemoglobin and deoxygenated hemoglobin via irradiating optical fibers;

a light detecting unit for detecting and amplifying the light passed through the object via detecting optical fibers;

a signal processing unit for calculating hemoglobin time change information of the oxygenated hemoglobin, deoxygenated hemoglobin and total hemoglobin in the body of the object from the signals detected by the light detecting unit, having noise detecting means for discriminating and detecting from the time variation information at least one type of noise attributed to obstacles with respect to the passing of light existing between the object and an end section of the optical fibers, and noise attributed to damage of the light irradiating unit; and a display unit for displaying the noise signals determined and detected by the signal processing means in a manner capable of identifying the kind of noise.

The noise detecting means is configured by the first noise detecting means for discriminating and detecting noise attributed to obstacles to the passing of light existing between the object and end face of optical fibers, and the second noise detecting means for discriminating and detecting noise attributed to deterioration of the light-irradiating unit.

In the first noise detecting means, standard deviation on time change of the detection signal value is calculated, and if the obtained standard deviation is more than the threshold value set in advance and gain in the light detecting means is more than the threshold value set in advance, the signals are determined to be noise signals.

Also, the second noise detecting means comprises means for acquiring time correlation value r with respect to time change information of the oxygenated hemoglobin and deoxygenated hemoglobin, and means for acquiring standard deviation values $SD_{ox}$, $SD_{dioxy}$ and $SD_{total}$ with respect to the oxygenated hemoglobin, deoxygenated hemoglobin and total hemoglobin, and if:

$r \leq r_0$, $SD_{doxy} \geq S_2 \times SD_{total}$, and $SD_{deoxy} \geq S_3 \times SD_{total}$ (in this regard, $r_0$, $S_2$ and $S_3$ are the values respectively appointed in advance), the signals are determined as noise signals.

BRIEF DESCRIPTION OF THE DIAGRAMS

BEST MODE FOR CARRYING OUT THE INVENTION

Hereinafter, an embodiment of the present invention will be described based on the attached diagrams.

Figure 4:
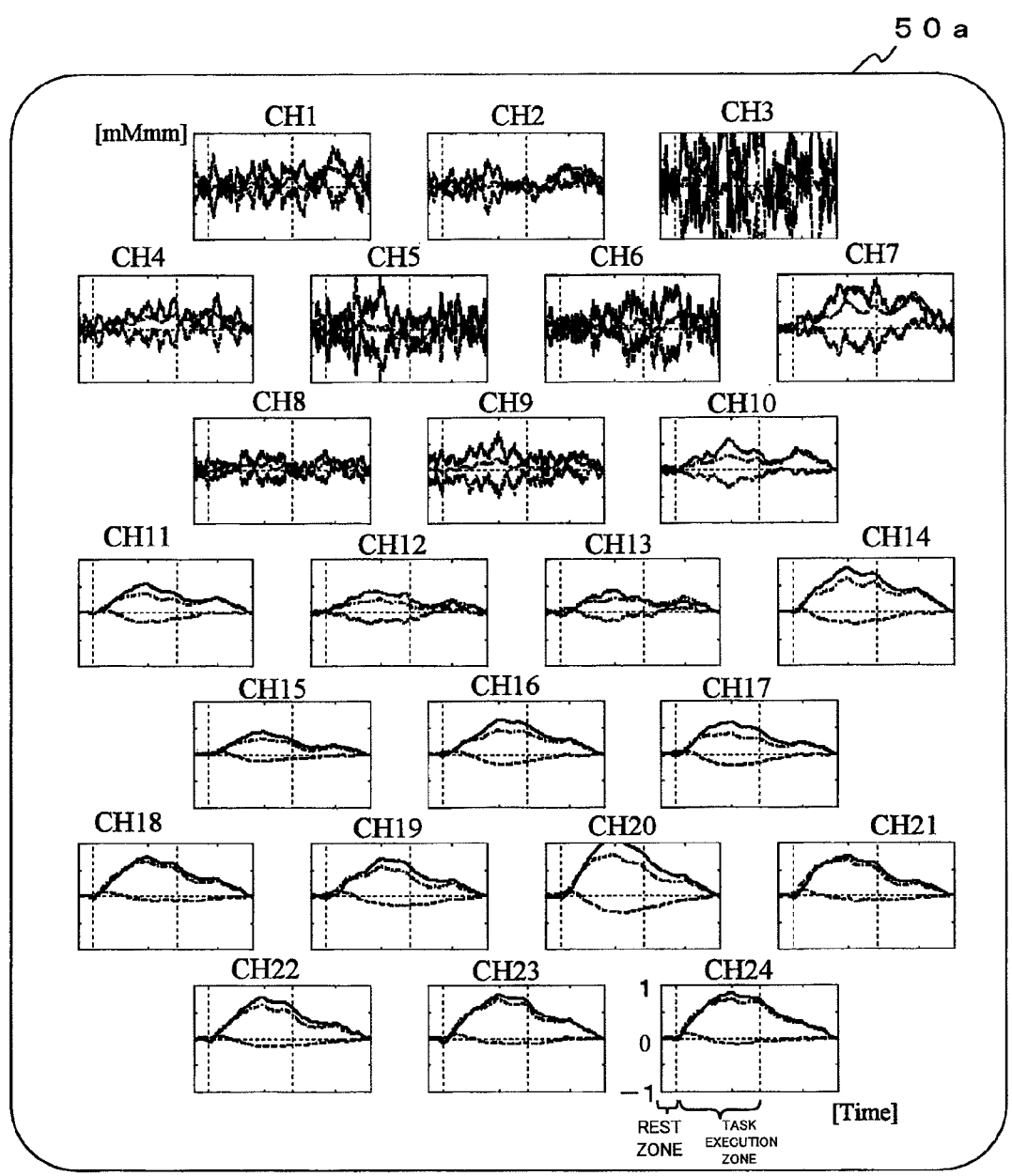
FIG. 4 is a diagram showing a display screen example of the hemoglobin variation signal waveforms of the biological photometric device shown in FIG. 1.
Figure 11:
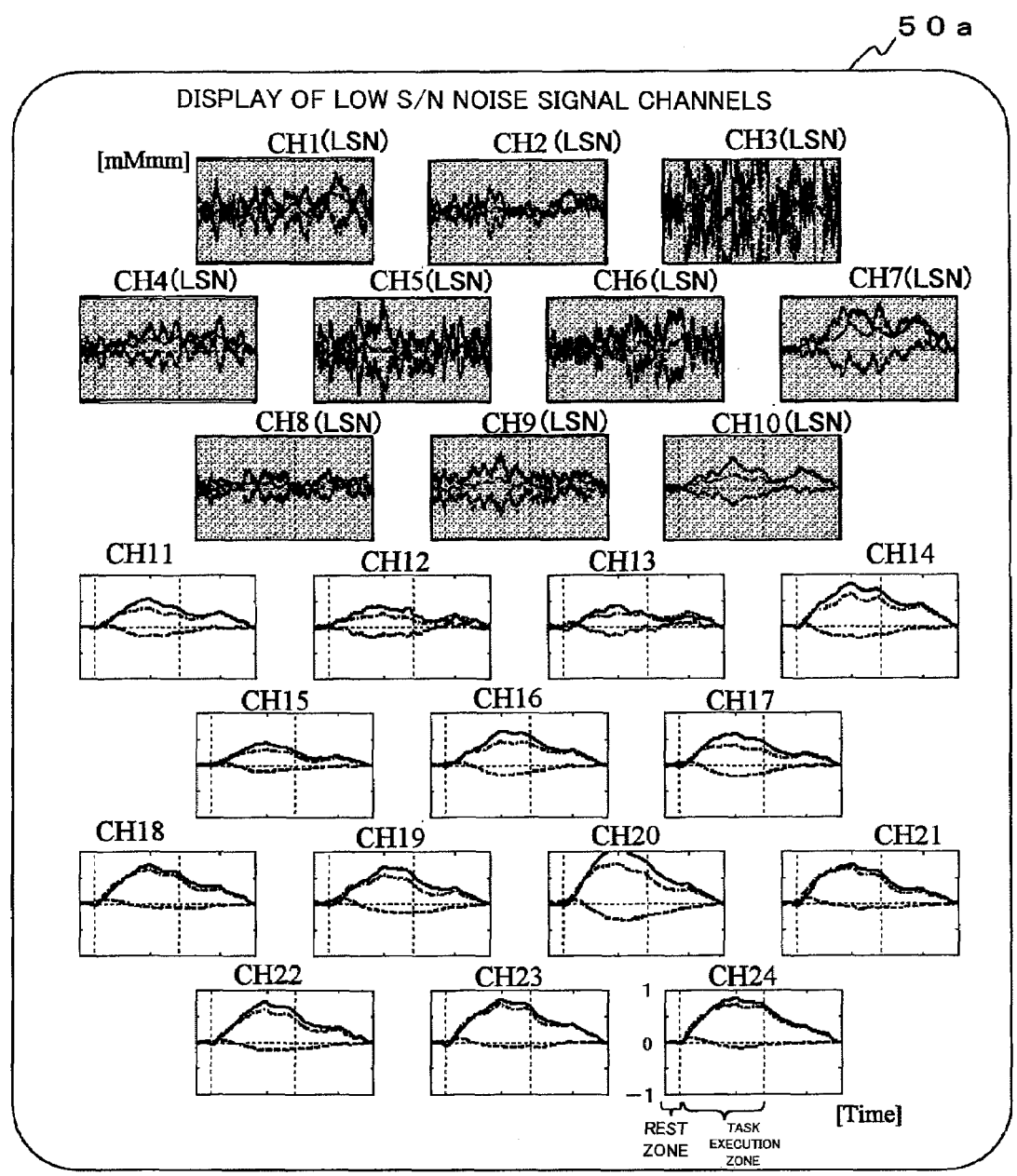
FIG. 11 is an explanatory diagram showing a display example of the channels for low S/N noise signals in the display screen of the hemoglobin variation signal waveforms illustrated in FIG. 4.
Figure 12:
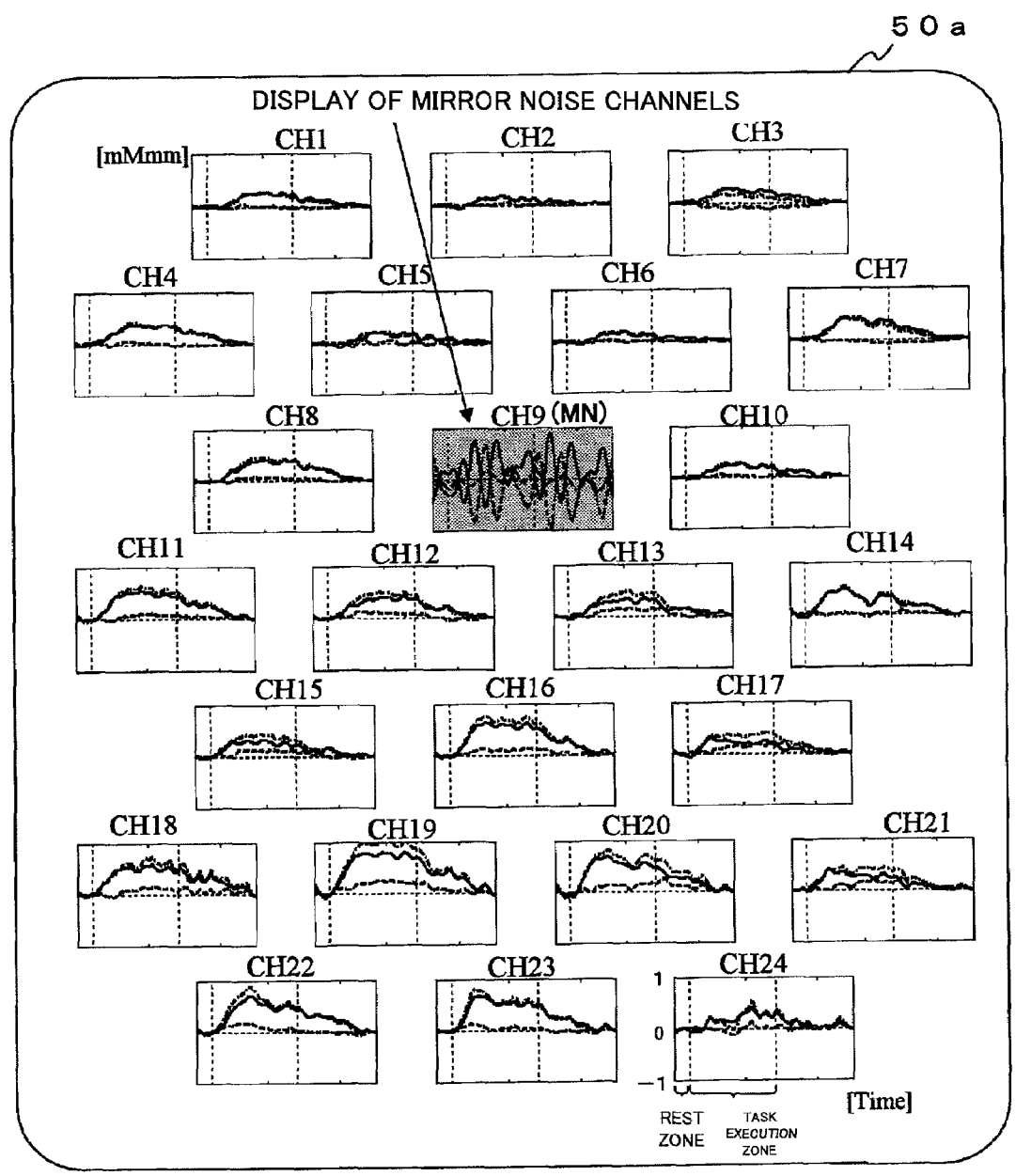
FIG. 12 is an explanatory diagram showing a display example of the channels for mirror noise signals in the display screen of the hemoglobin variation signal waveforms illustrated in FIG. 4.

First, a general configuration of the biological photometric device of the first embodiment related to the present invention will be described using the block diagram of FIG. 1. In the present embodiment, while the device having 12 channels for measuring 12 measure points (channels) 1~12 are illustrated in FIGS. 1 and 2 and a display example of the device having 24 channels are illustrated in FIGS. 4, 11 and 12 for the sake of the convenience in diagrammatic representation, the present invention is applicable to biological photometric devices provided with an arbitrarily numbers of measurement channels.

Figure 1:
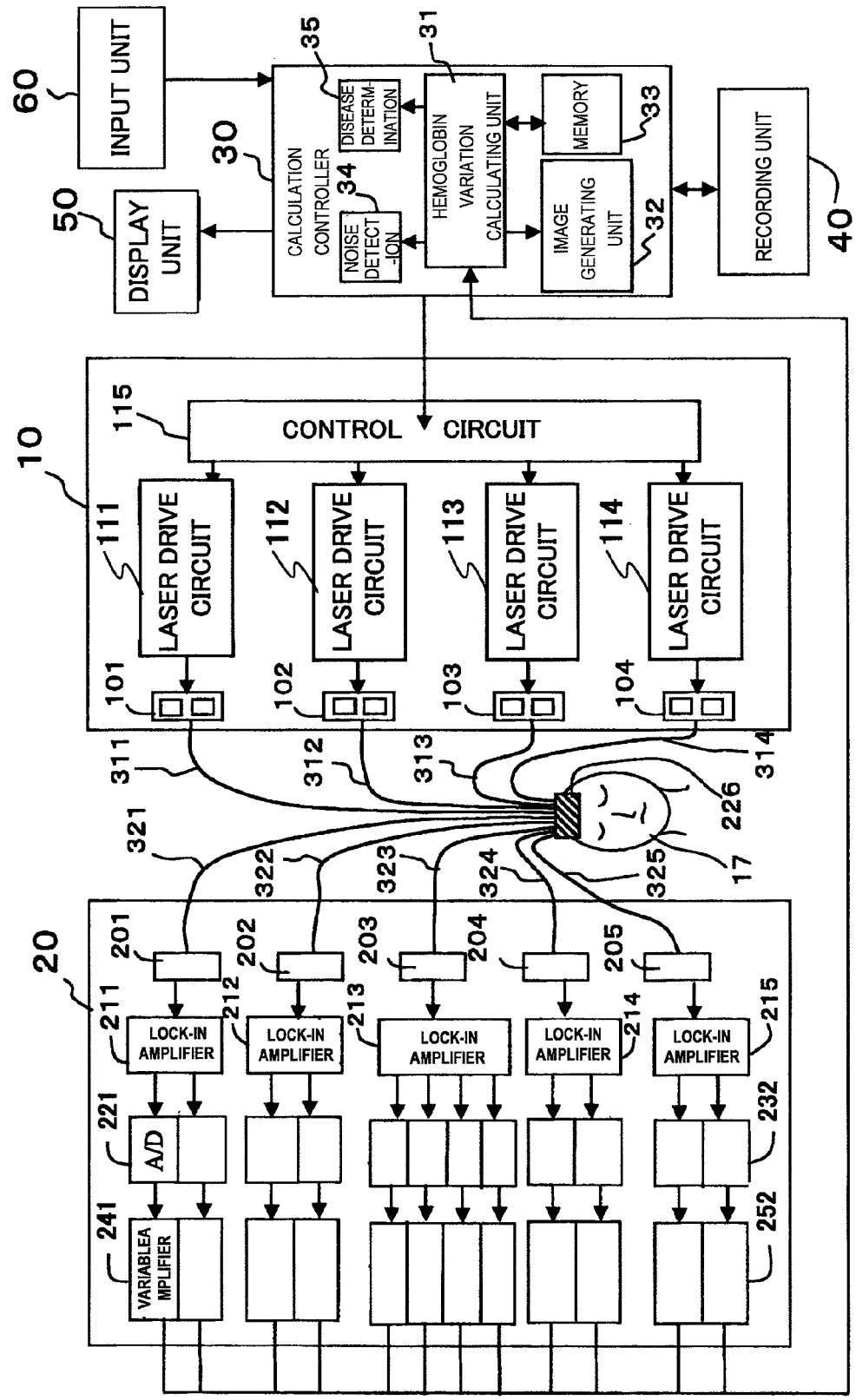
FIG. 1 is a block diagram showing a general configuration of a biological photometric device of the first embodiment of the present invention.
Figure 2:
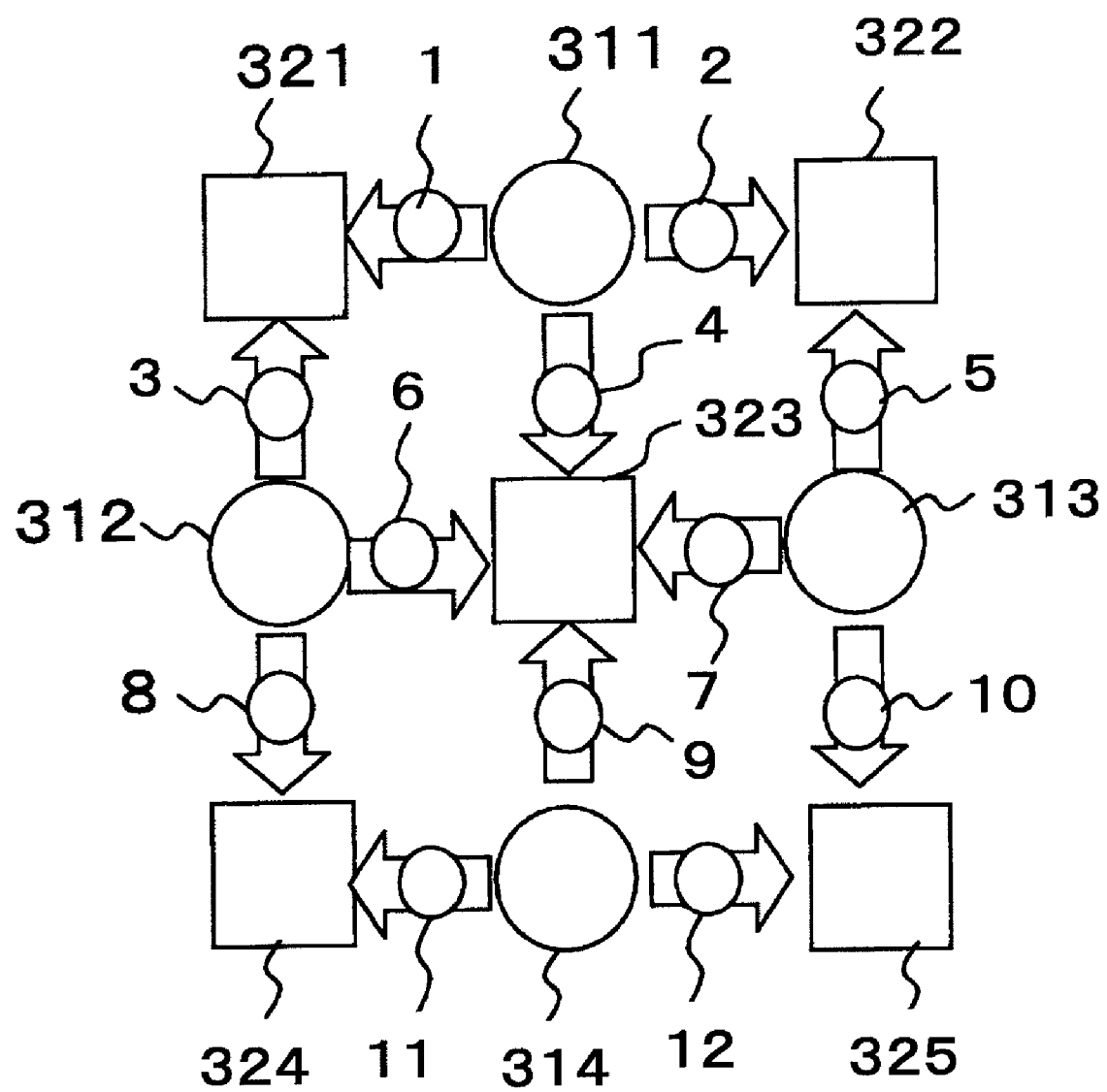
FIG. 2 is a diagram showing relationship between arrangement and measure points (channels) of irradiating optical fibers and detecting optical fibers related to the biological photometric device shown in FIG. 1.

The biological photometric device of the present invention has light-irradiating module 10, light-detecting module 20 and calculation controller 30 comprising CPU, and recording unit 40 for storing obtained data, display unit 50 and input unit 60 for receiving commands from an operator are connected to calculation controller 30 as shown in FIG. 1. In the above-described configuration, the respective units perform calculation, creation of charts and images and determination via CPU provided in calculation controller 30.

In light-irradiating module 10, laser modules 101~104, laser drive circuits 111~114 respectively connected thereto and control circuit 115 for controlling laser drive circuits 111~114 are disposed. Each of laser modules 101~104 includes two laser diodes for emitting light having 780 nm and 830 nm of wavelength. By the respective laser drive circuits 111~114 providing drive current of a predetermined frequency and current density with respect to the respectively connected laser module, the respective laser modules produce lights that are modulated by respectively different modulation frequency having a predetermined luminance intensity, with respect to other laser modules. In addition, the wavelength of laser modules 101~104 is not limited to the combination of 780 nm and 830 nm.

To each of laser modules 101~104, irradiating optical fibers 311~314 are connected for interblending and propagating the light produced by two laser diodes, guiding the light to a measuring region of object 17 and irradiating the light from an incoming end face. The outputting end face of irradiation optical fibers 311~314 are disposed in a way that they are brought into contact with the body surface of object 17 being firmly applied by probe holder 226.

To probe holder 226, 5 detecting optical fibers 321~325 are disposed so that they are alternately positioned with respect to the position in the outputting end surface of 4 irradiating optical fibers 311~314. The incoming end surface of detecting optical fibers 321~325 are also disposed in a way so that they are brought into contact with the body surface of object 17 being firmly applied by probe holder 226.

The light outputted toward object 17 from the end surface of irradiating optical fibers 311~314 is passed through 12 measure points 1~12 of object 17, inputted to the end surface of detecting optical fibers 321~325, and propagated to the inside of detecting optical fibers 321~325. In addition, while configuration matrix of the outputting end surface of irradiating optical fibers 311~314 and the input end surface of detecting optical fibers 321~325 is 3×3 due to the diagrammatic representation of the case for 12 channel measurement being illustrated in FIG. 2, the configuration matrix in the case of performing 24 channel measurement is 4×4 and 8 wires each of irradiating optical fibers and detecting optical fibers are disposed.

Light-detecting module 20 has avalanche photodiodes 201~205, lock-in amplifiers 211~215, A/D converters 221~232 and continuous variable amplifiers 241~252. Avalanche photodiodes 201~205 convert the light propagated by detecting optical fibers 321~325 respectively into voltage signals. Lock-in amplifiers 211~215 separate and retrieve the signals with respect to the 12 measure points 1~12 based on modulation frequency of the signals outputted from photodiodes 201~205. Out of photodiodes 201~205, lock-in amplifiers 211, 212, 214 and 215 for being connected to photodiodes 201, 202, 204 and 205 to which the light of detecting optical fibers 321, 322, 324 and 325 are inputted respectively output two signals, and photodiode 203 to which the light of detecting optical fiber 323 is inputted outputs four signals. The reason for this is that, in arrangement of irradiating optical fibers 311~314, detecting optical fibers 321~325 and measure points 1~12 shown in FIG. 2, that the respective detecting optical fibers are made to take in the signals that are adjacent thereto. The output signals with respect to measure points 1~12 outputted from lock-in amplifiers 211~215 are respectively converted into digital signals by A/D converters 221~232.

Continuous variable amplifiers 241~252 respectively set the gain according to the intensity of output signals with respect to measure points 1~12 received from A/D converters 221~232. By such operation, output signals of measure points 1~12 are respectively amplified to the previously set signal intensity, and transferred to calculation controller 30.

Calculation controller 30 has hemoglobin variation calculating unit 31, image generating unit 32, memory 33 and noise detecting unit 34. Hemoglobin variation calculating unit 31 obtains oxygenated hemoglobin variation $\Delta C_{oxy}$ and deoxygenated hemoglobin variation $\Delta C_{deoxy}$ from the signals of two wavelengths received from variable amplifiers 241~252 through solving the simultaneous equations of the formulas (1) and (2) below. Further, total hemoglobin variation $\Delta C_{total}$ is obtained from oxygenated hemoglobin variation $\Delta C_{oxy}$ and deoxygenated hemoglobin variation $\Delta C_{deoxy}$ using the formula (3). These calculations are performed by CPU.

$$-\ln(I_{act}(780)/I_{base}(780))=\epsilon_{oxy}(780)\Delta C_{oxy}L+\epsilon_{deoxy}(780)\Delta C_{deoxy}L \quad (1)$$

$$-\ln(I_{act}(830)/I_{base}(830))=\epsilon_{oxy}(830)\Delta C_{oxy}L+\epsilon_{deoxy}(830)\Delta C_{deoxy}L \quad (2)$$

$$\Delta C_{total}=\Delta C_{oxy}+\Delta C_{deoxy} \quad (3)$$

In this regard, however, in the formula (1) and (2), $I_{act}(\lambda)$ and $I_{base}(\lambda)$ respectively represent signal intensity of wavelength $\lambda$ nm at task execution state and rest state (output power of light detecting module 100), $\epsilon_{oxy}(\lambda)$ and $\epsilon_{deoxy}(\lambda)$ respectively represent molecular extinction coefficient of oxygenated and deoxygenated hemoglobin at wavelength $\lambda$ nm, and L represents light path length. In the explanations below, hemoglobin variation is an inclusive name for oxygenated hemoglobin variation $\Delta C_{oxy}$, deoxygenated hemoglobin variation $\Delta C_{deoxy}$ and total hemoglobin variation $\Delta C_{total}$.

Figure 3:
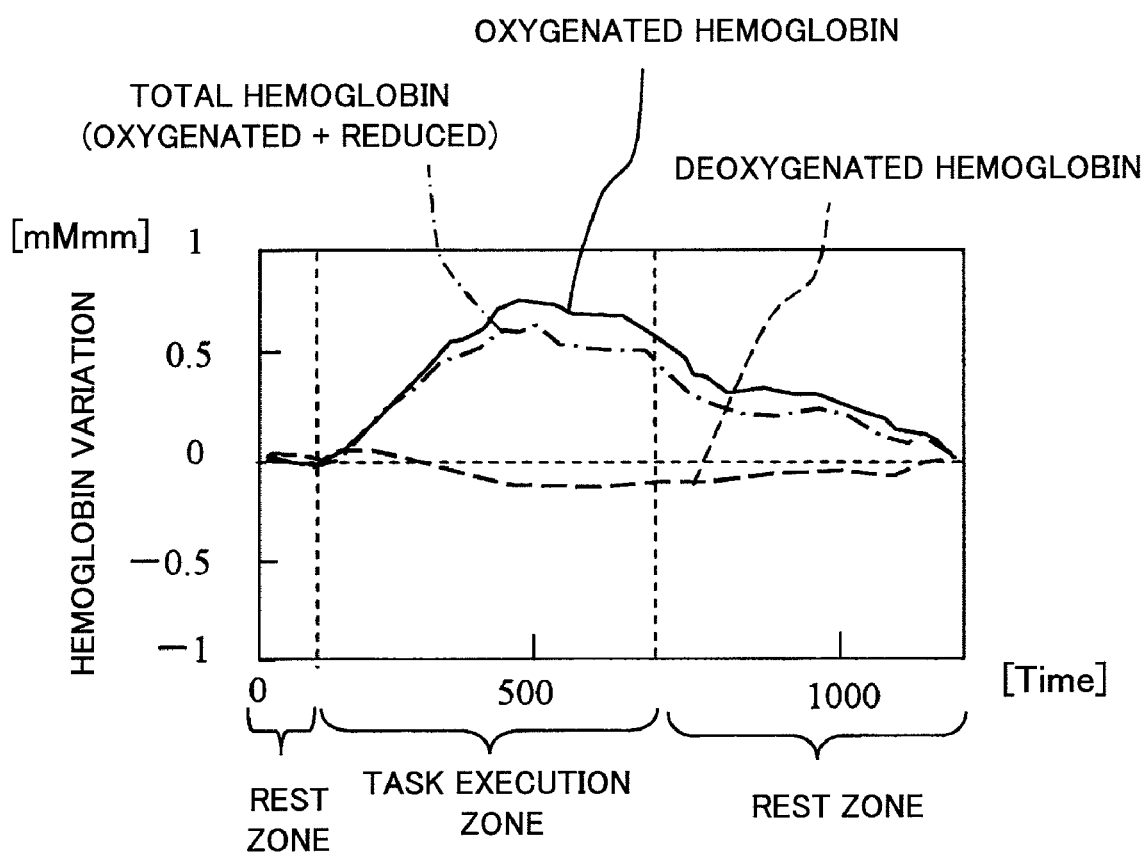
FIG. 3 is a chart showing waveforms of the hemoglobin variation signals obtained from detecting signals by the biological photometric device illustrated in FIG. 1.

From the obtained oxygenated hemoglobin variation $\Delta C_{oxy}$, deoxygenated hemoglobin variation $\Delta C_{deoxy}$ and total hemoglobin variation $\Delta C_{total}$, waveform chart data of hemoglobin variation (mMmm) with respect to the time axis in each channel (measure point) are created by hemoglobin variation calculating unit 31 as shown in FIG. 3. More specifically, 12 chart data are created, then the created chart data with respect to the respective channels (measure points) are outputted to display unit 50, and displayed on display screen 50a of display unit 50 in arrangement corresponding to the arrangement of measure points 1~12 shown in FIG. 2. Meantime, FIG. 4 illustrates an example of graphical representation of the measurement result in the case of configuration for performing 24-channel measurement of irradiating optical fibers and detecting optical fibers as a 4×4 arrangement matrix. The obtained information such as data of hemoglobin variation or hemoglobin variation charts is stored in memory 33.

Image generating unit 32 of calculation controller 30 generates a topography image of a measuring region by a well-known method using the hemoglobin variation calculated by hemoglobin variation calculating unit 31, and displays it on display 50. Also, disease-determining unit 35 determines the kind of disease by comparing the pattern of the hemoglobin variation calculated by hemoglobin variation calculating unit 31 to a predetermined template using the well-known method described in Patent Document 2.

Patent Document 2: JP-A-2003-275191

Noise detecting unit 34 disposed in calculation controller 30 determines whether hemoglobin variation signals with respect to the respective channels (measure points) calculated in hemoglobin variation calculating unit 31 are noise signals or not. In the present embodiment, whether hemoglobin variation signals are low noise signals/mirror noise signals or not, and whether spike noise signals are included or not, are respectively determined.

The low S/N noise signals here are high-frequency signals that appear on the measurement signals in the case that very little light is detected by photodiodes 201~205 such as the case that the aperture of the outputting end face of irradiating optical fibers 311~314 or detecting optical fibers 321~325 is covered by an obstacle with respect to the light except a skin of an object such as, for example, a hair of the object. And the low S/N noise signals take the form as, for example, channels 1~10 in the chart shown in FIG. 4.

Mirror noise signals are the noise that appear in the case that, out of two laser diodes having different wavelengths that are built in laser modules 101~104, one laser diode had a damage or breakage, or only one light of the wavelength is detected in photodiodes 201~205 due to deterioration of the light irradiating system including operation defect of the laser diode drive circuit. More specifically, when the light irradiating system of one wavelength is damaged or does not operate normally, hemoglobin variation calculating unit 31 calculates $\Delta C_{oxy}$ and $\Delta C_{deoxy}$ which are the solutions of formula (1) and formula (2), since one of the two values of $I_{act}(780)$ or $I_{act}(830)$ becomes close to 0. Therefore, mirror noise can be detected attributed to the reflection of mirror image relationship in the calculation result, that is when oxygenated hemoglobin $\Delta C_{oxy}$ increases deoxygenated hemoglobin $\Delta C_{deoxy}$ decreases, and when oxygenated hemoglobin $\Delta C_{oxy}$ decreases and deoxygenated hemoglobin $\Delta C_{deoxy}$ increases.

Spike noise signals are the spike-like noise signals that appear attributed to gaps generated between an object and an aperture of the optical fibers by the movement of the object during measurement, or by displacement of applied outputting end surface of the irradiating optical fibers 311~314 or the incoming end surface of the detecting optical fibers 321~325 with respect to the body surface of the object.

Figure 5:
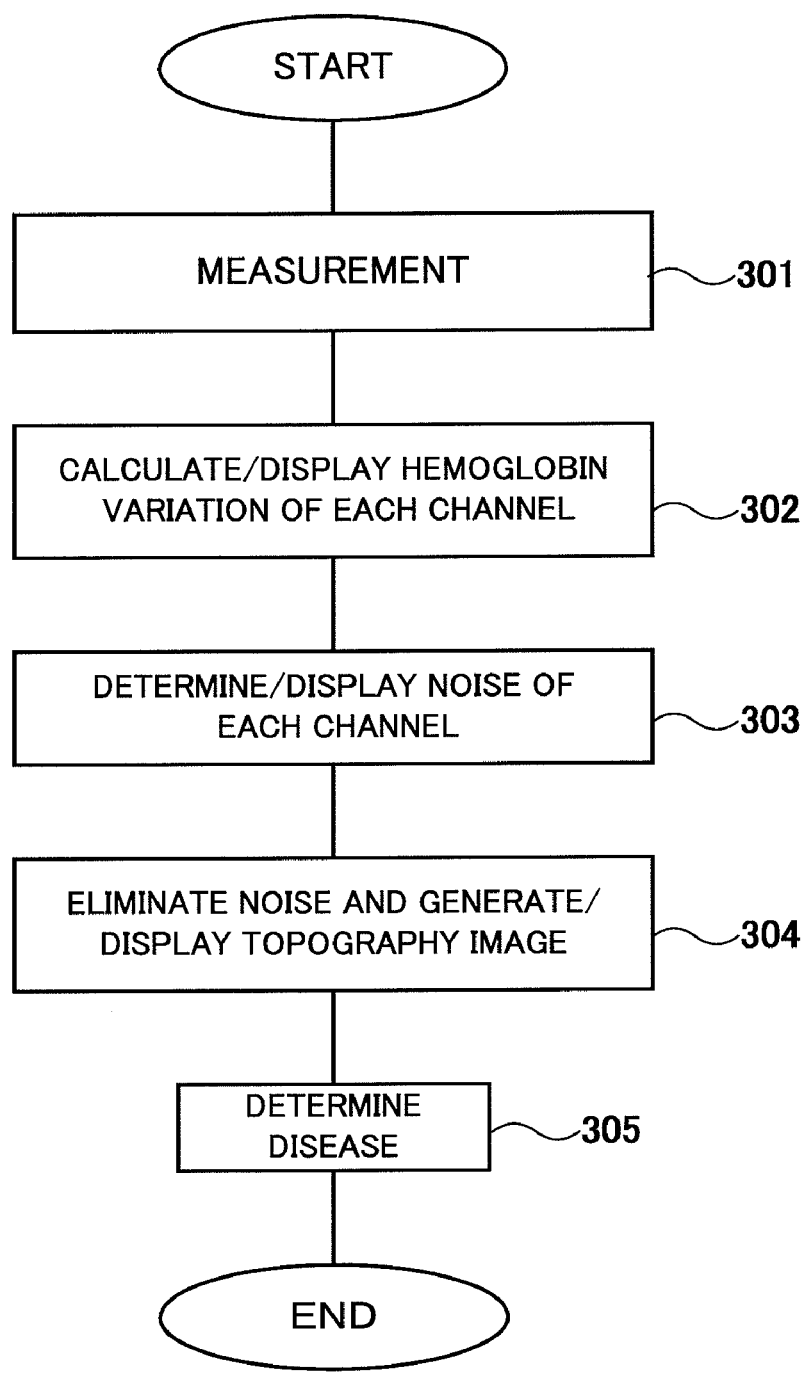
FIG. 5 is a flow chart showing an entire operation of the biological photometric device of the present invention.

Next, an operation of the biological photometric device will be described using the flow chart in FIG. 5. By light irradiating module 10 being operated by calculation controller 30, the light is irradiated from irradiating optical fibers 311~314 to object 17, and a part of the light passed through the living body is retrieved by detecting optical fibers 321~325. The retrieved light is electrically signal-processed by light detecting module 20, and time variation of the hemoglobin in the predetermined region of object 17 is measured (step 301).

During the measuring period, an operator sequentially indicates the complete rest, task execution and rest with respect to object 17, and the signals with respect to the complete rest zone, task execution zone and rest zone are obtained as shown in FIG. 3. The obtained signals are converted into hemoglobin variation as mentioned above by hemoglobin variation calculating unit 31, and the time variation chart of the hemoglobin variation with respect to the respect channels are displayed on display screen 50a of display unit 50. Also, the data converted into hemoglobin variation by hemoglobin variation calculating unit 31 are stored in memory 33 (step 302).

Next, determination of noise is executed by noise detecting unit 34 using the process to be described later (step 303). More specifically, in this step 303, noise detecting unit 34 determines whether the hemoglobin variation data of the respective channels being read out from memory 33 of calculation controller 30 is noise or not, or whether noise is included in the data or not. When it determines that the signals of a specific channel is noise, or noise is included in a specific channel, noise detecting unit 34 imparts a symbol to the data, for example, a flag to indicate that the signals are noise, or noise is included in the signals. Based on the indication, image-generating unit 32 displays notification of noise to the operator with the application of the display form to be described later on the chart displaying the signals being noise or the signals including noise.

Then a tomographic image is generated in image generating unit 32 under the condition that the hemoglobin variation signals of the channel determined as noise is eliminated or not used, and the generated topography image is displayed on display unit 50 (step 304).

After that, in disease determining unit 35, disease with respect to object 17 is determined from the hemoglobin variation of normal channels while hemoglobin variation information of the channel that is determined as noise is eliminated or not used, and the result thereof is displayed on display 50 (step 305).

Next, the process of step 303 in the noise detecting unit 34 will be described in detail using FIGS. 6 and 7. First, in noise detecting unit 34, whether the hemoglobin variation signals of the respective channels is a low S/N noise signals or not is determined by the process shown in the flow chart of FIG. 6. This process is for determining whether the signals are low S/N noise signals or not, by focusing attention on the fact that low S/N noise signals have high frequency compared to the signals of the normal channels 11~24 and that low S/N noise signals indicate a waveform that differs little in the complete rest zone and in the task execution zone. Such waveform of the low S/N noise signals is attributed to the fact that it gets amplified by a large gain (gain value) in continuous amplifiers 221~225 since the output signal value of photodiodes 201~205 is small.

In order to determine whether the hemoglobin variation signals are low S/N noise signals or not, noise detecting unit 34 obtains the hemoglobin variation signal waveform data of the respective channels from hemoglobin variation calculating unit 31 or memory 33 (step 501). While it is mentioned that the hemoglobin variation signals are provided from hemoglobin variation calculating unit 31 or memory 33, it is possible to decide from which unit the hemoglobin variation signals should be provided, by considering the determination velocity of noise detecting unit 34 or real-time aspect of the time up to the display of the final result.

Following step 501, standard deviation value SD of the complete rest zone set in advance with respect to the respective signal waveform data of the variation of oxygenated hemoglobin, deoxygenated hemoglobin and total hemoglobin obtained in the respective channels is calculated, and gain value being set during signal measurement is obtained at variable amplifiers 241~252 (step 503).

Noise detecting unit 34 searches for the channels which fulfill the condition for determination that at least one of the respective standard deviation value SD of the variation of oxygenated hemoglobin, deoxygenated hemoglobin and total hemoglobin of the respective channels is more than the predetermined threshold S0, and that gain value AMP of the variable amplifier is more than the predetermined threshold A0 (step 504), and determines the signals of the channels which fulfill those conditions as low S/N noise signals (step 505). At the same time, it determines that the signals wherein the standard deviation value SD is less than the predetermined value S0 and/or the gain value of the variable amplifier is less than a predetermined value A0 are low S/N noise signals (step 506). Threshold values S0 and A0 can be the values set in advance by experiment and incorporated in a determination algorithm as fixed values, or the device can be configured in a way that the operator can input an arbitrarily value from input unit 60 shown in FIG. 1 according to the volume of hair or thickness of bones of the object. In the present embodiment, as threshold value S0 of standard deviation value SD and threshold value A0 of gain value AMP of a variable amplifier, values S0=0.02 and A0=3000 that are experimentally set by the inventor of the present invention are used as criterion value of the low S/N noise signals.

Figure 8:
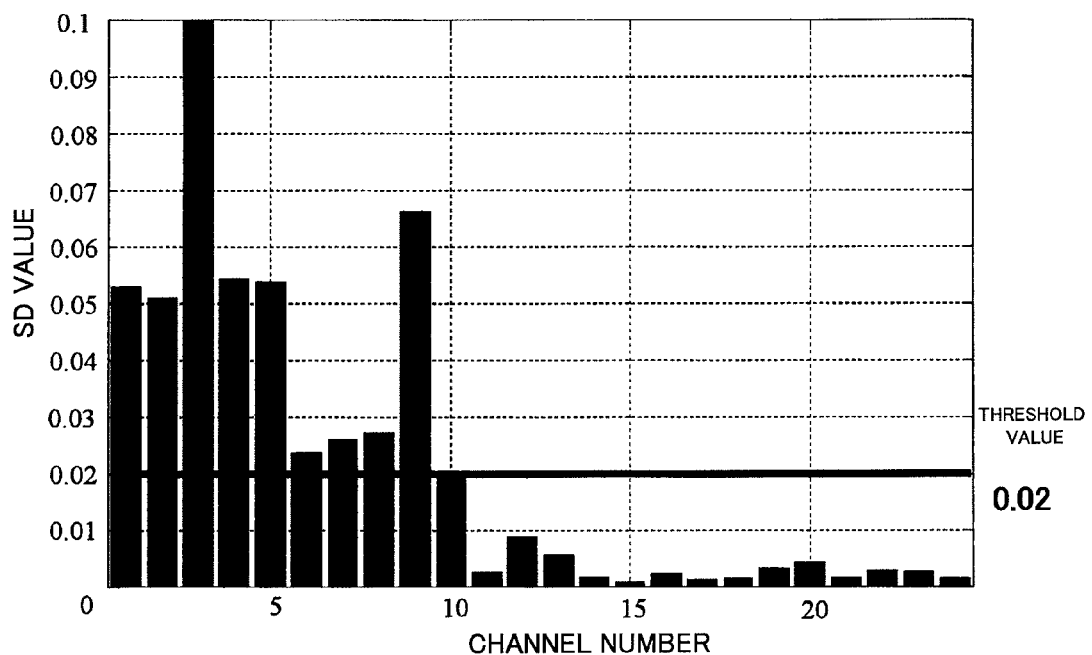
FIG. 8 is a chart showing standard deviation SD calculated in step 502 with respect to each channel in the flow chart illustrated in FIG. 6.
Figure 9:
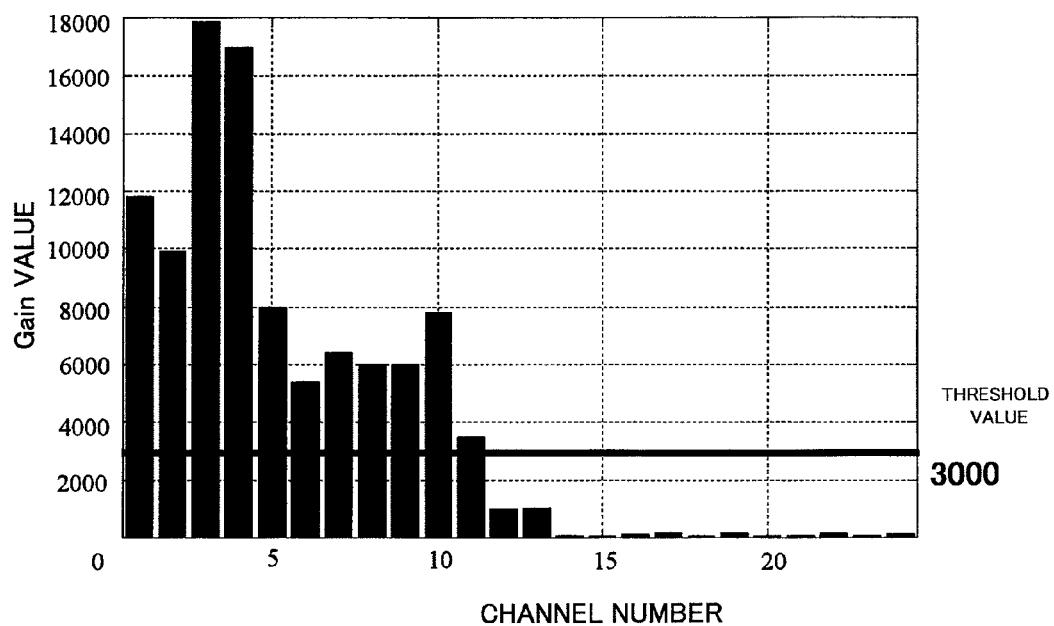
FIG. 9 is a chart showing gain value of the variable amplifier with respect to each channel obtained in step 503 in the flow chart illustrated in FIG. 6.

In FIG. 8 and FIG. 9, standard deviation SD of a complete rest zone and the gain value AMP of the variable amplifier thereof are illustrated while taking an example in which the hemoglobin variation chart of 1~24 channels are represented as the respective waveforms shown in FIG. 4. When FIG. 4 is compared to FIGS. 8 and 9, channels 1~10 having large distortion in the waveform has standard deviation value SD which is more than the above-mentioned criterion value 0.02 and gain value AMP of the variable amplifier which is more than the above-mentioned criterion value 3000. In other words, channels 1~10 that are low S/N noise signals indicate a pattern, when compared to the normal channels 11~24, that standard deviation value SD and the gain value of a variable amplifier show large values. Therefore, it is possible to determine whether output signals of the measurement channel are low S/N noise signals or not by setting standard deviation value SD and threshold A0 of gain value of the variable amplifier at a proper set value (for example, S0=0.02 and A0=3000).

Figure 6:
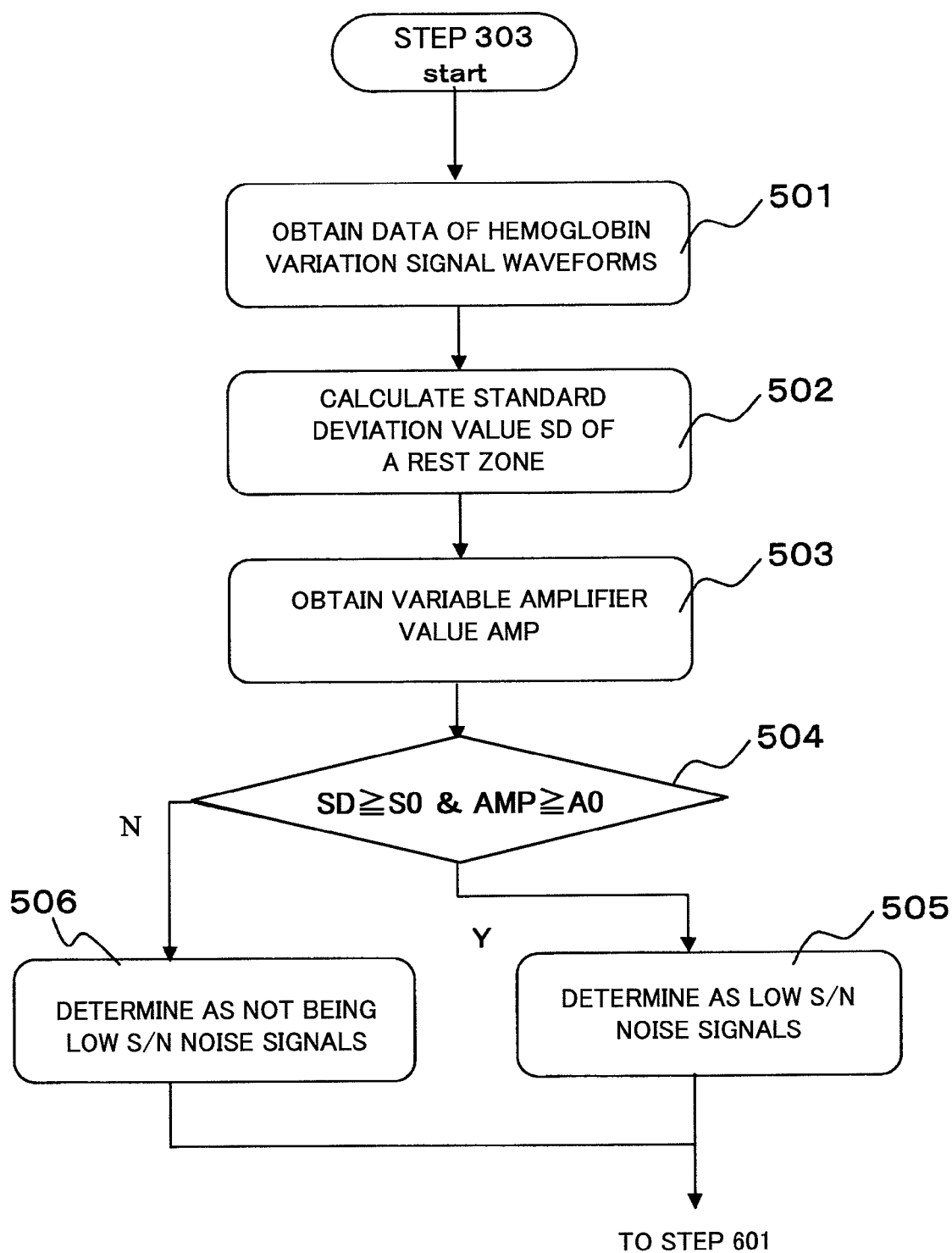
FIG. 6 is a flow chart showing a procedure for determining low S/N noise signals in step 303 in the flow chart illustrated in FIG. 5.
Figure 7:
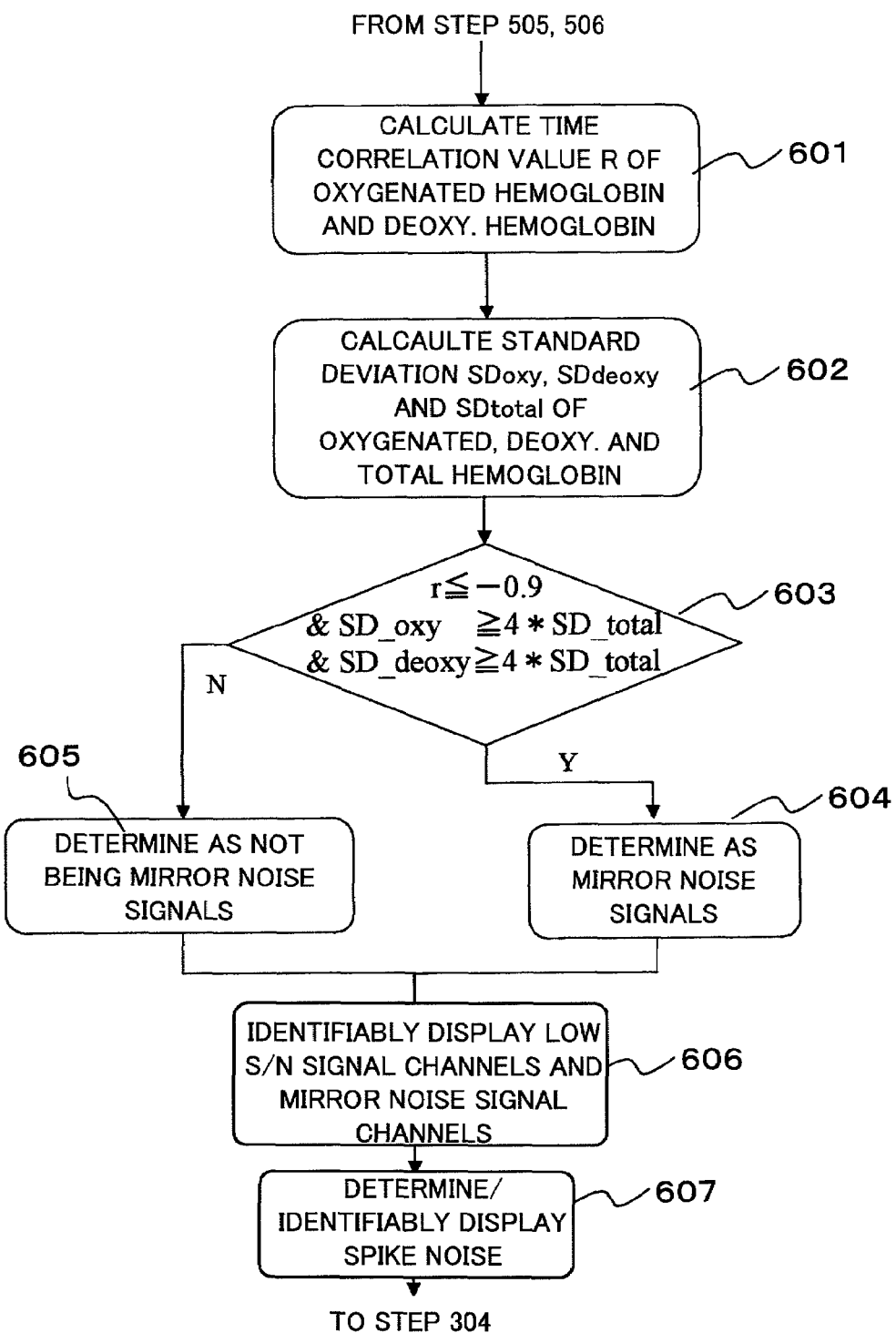
FIG. 7 is a flow chart showing a procedure for determining mirror noise signals in step 303 in the flow chart illustrated in FIG. 5.
Figure 10:
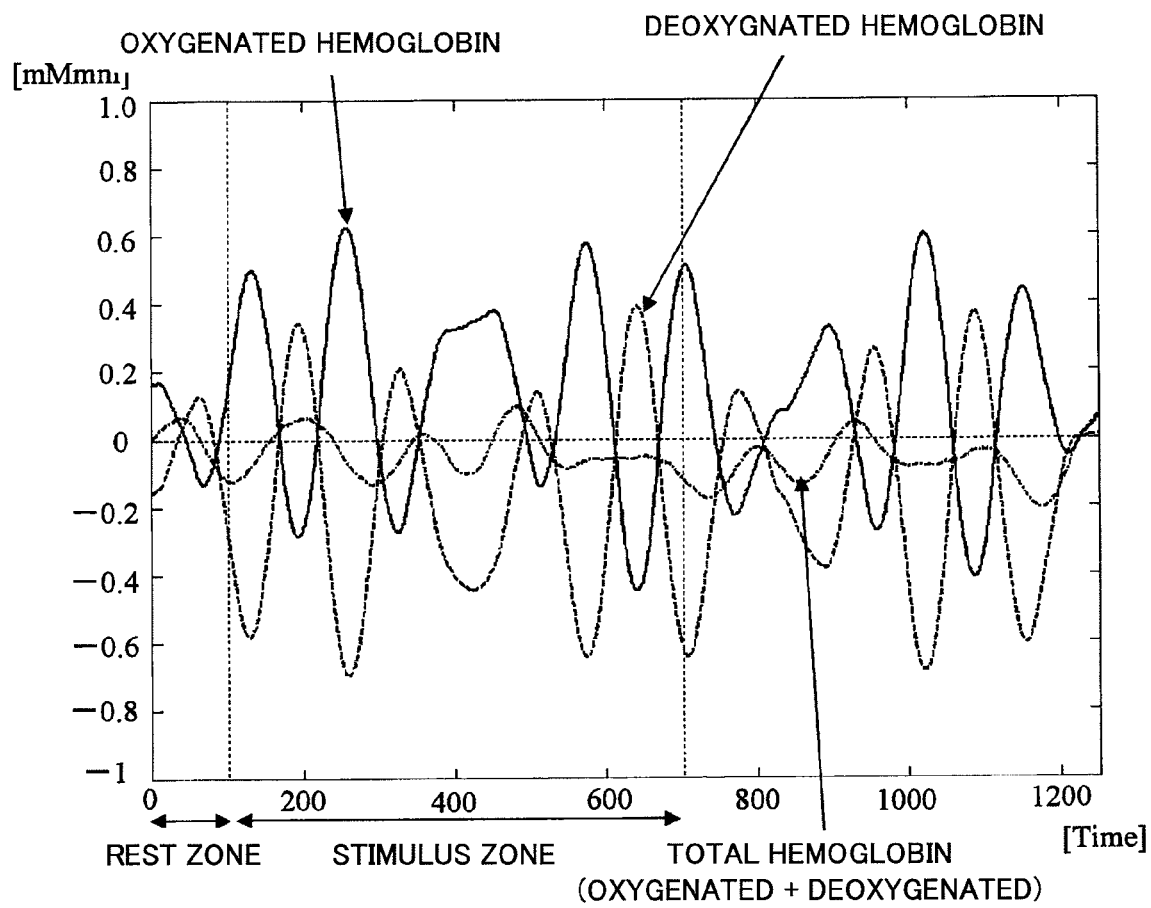
FIG. 10 is a diagram showing an example of mirror noise waveforms.

Next, followed by step 505 and step 506 in FIG. 6, determination of mirror noise is executed in noise detecting unit 34 by the process of a flow chart in FIG. 7. An example of mirror noise signals are shown in FIG. 10(*a*). While FIG. 10(*a*) shows an example of the signal waveform of mirror noise, the total hemoglobin has a moderate signal waveform, and the oxygenated hemoglobin variation signals and deoxygenated hemoglobin variation signals have mirror-image relationship. Thus the total hemoglobin variation shows a value close to 0. Given this factor, determination of mirror noise can be executed by obtaining stability factor of the waveform from time correlation value r indicating similarity of the oxygenated hemoglobin variation and deoxygenated hemoglobin variation, and from standard deviation of the oxygenated hemoglobin variation, deoxygenated hemoglobin variation and total hemoglobin variation. Meantime, FIG. 10(*b*) shows the calculation result of standard deviation value SD, gain value AMP of variable amplifier, time correlation value r of the oxygenated hemoglobin and deoxygenated hemoglobin, and standard deviation value of the oxygenated hemoglobin, deoxygenated hemoglobin and total hemoglobin with respect to the entire measurement period, based on the waveforms shown in FIG. 10(*a*). Detailed description on the method for obtaining time correlation value r is omitted here, since it is disclosed in various documents.

First, in a flow chart of FIG. 7, with respect to the output signals of the respective channels, time correlation value r is calculated between the waveform of oxygenated hemoglobin variation $\Delta C_{oxy}$ and the waveform of deoxygenated hemoglobin variation $\Delta C_{deoxy}$ with respect to a predetermined measurement period within the entire measurement period formed by complete rest zone, task execution zone and complete rest zone (step 601). As for the predetermined measurement period, the period in which the characteristic of the signal waveform reaches maximum state, for example, the task execution is suitable, and this measurement period can be incorporated in the mirror noise determination algorithm in noise detecting unit 34. It is also possible to configure the device so that the operator can arbitrarily designate and input the desired time range using input unit 60.

Next, standard deviation values $SD_{oxy}$, $SD_{deoxy}$ and $SD_{total}$ with respect to the oxygenated hemoglobin variation, deoxygenated hemoglobin variation and total hemoglobin variation within the above-mentioned predetermined measurement period are calculated (step 602).

Correlation value r indicates that the closer the absolute value is to 1 the more similar both waveforms are, and when the direction of the waveform is the same it is a positive sign and when the direction of waveform is inverted it is a negative sign. Given this factor, whether the obtained correlation value r is close to −1 or not is determined by comparison from predetermined value r0 (r≦r0). Further, a degree of stability is acquired from standard deviation values $SD_{oxy}$, $SD_{deoxy}$ and $SD_{total}$ by the formulas (4) and (5) below (step 603).

$$SD_{oxy} \geq S_2 \times SD_{total} \quad (4)$$

$$SD_{deoxy} \geq S_3 \times SD_{total} \quad (5)$$

Here, $S_2$ and $S_3$ are multiplication values and may be set in advance as the appointed values in an algorithm, or these values can be set so that the operator inputs arbitrary values using input unit 60. Also, as for S2 and S3, equal values, for example, S2=S3=4 may be used, or different values may be used. In the same manner, as for the above-mentioned r0, while an example using r0=−0.9 is illustrated here as a set value in advance, it also is possible to variably set other values which are close to −1 such as −0.8.

When the above correlation value determination formula is r≦r0 and both formulas (4) and (5) for indicating the degree of stability are satisfied, the output signals of the channel thereof are determined as mirror noise (step 604). On the other hand, when the correlation value determination formula r≦r0 of the correlation value is not satisfied or at least one of the formulas (4) and (5) are not satisfied, the output signals of the channel thereof are determined not to be mirror noise (step 605). When the values shown in FIG. 10(*b*) calculated with respect to the waveform signals shown in FIG. 10(*a*) are applied to the above-mentioned determination criteria, the waveforms are determined as mirror noise.

It is desirable that the determination result of low S/N noise and/or mirror noise is displayed in an illustrative embodiment that is respectively recognizable to the operator as shown in FIGS. 11 and 12. There are several illustrative embodiments for indicating low S/N noise and/or mirror noise to the operator. One of them is to color the background of a chart of the channels determined as low S/N noise or mirror noise. In this case, it is effective to display by changing the color of the background in the rectangle graph region so that the channels of low S/N noise can be distinguished from the channels of mirror noise channel on the display screen. Further as another illustrative embodiments, identification symbols or letters for indicating the kind of noise are effective when added to the display screen near the chart of the channels determined as low S/N noise or mirror noise upon being displayed. For example, "LSN" which is an abbreviation for low S/N noise may be added near the channel determined as low S/N noise, and "MN" which is an abbreviation for mirror noise may be added for the channels determined as mirror noise, as shown in FIGS. 11 and 12. These illustrative embodiments can be easily implemented by incorporating the display program into the software in advance.

Noise detecting unit 34 also determines about the spike noise whether the hemoglobin variation signals are precipitous or not by searching if there is a part wherein the derivative value with respect to the time change of the signal value is more than the predetermined value over the entire measurement period of the respective channels. Detailed description on this determination method will be omitted here since it is a well-known method disclosed in, for example, the previously mentioned Patent Document 1 (WO 03/002004) filed by the present applicant prior to the present application. Additionally for the channel determined as spike noise, the identification method by coloring the background which uses the similar chart as the display method for displaying the determination result of low S/N noise and/or mirror noise shown in FIGS. 11 and 12 can be applied. In the case that low S/N noise, mirror noise and spike noise all appear at the same time during the same measurement period, it is better to use different colors on each background. If it seems difficult to identify them by only making the background colors different, the letters "SPN" for abbreviation of spike noise may be displayed near the chart.

By using the above-mentioned display method, the operator can easily grasp which channels are low S/N noise, mirror noise and spike noise.

The display of the above-mentioned three kinds of noise detecting results indicates the condition that the end surface of optical fibers 311~314 and 321~325 are covered by the hair of object 17 (low S/N noise), the condition that one of the two laser diodes in the laser module is either operationally defective or damaged (mirror noise), or the condition that either the object moved during the measurement or displacement was generated between the object and the optical fibers as they were brought into contact (spike noise), whereby enabling execution of processing according to the respective condition. That is, the operator can recognize that hair stuck between the irradiating optical fiber or the detecting optical fiber and the object needs to be removed when low S/N noise is detected, the laser diode needs to be replaced or the drive circuit needs to be inspected when mirror noise is detected, and the operator needs to instruct the object not to move when spike noise is detected.

In the present embodiment, in step 304, highly accurate topographies are displayed on display 50 since they are generated using the signals from which the signals of noise channels are eliminated, whereby enabling the operator to accurately grasp the condition of the object. Also in the present embodiment, since disease detection unit 35 executes disease determination using the signals from which the signals of noise channels are eliminated, determination with high accuracy can be executed without being influenced by noise.

Next, the second embodiment of the biological photometric device related to the present invention will be described.

In the biological photometric device of the second embodiment, noise detecting unit 34A has a function for generating the hemoglobin variation signal waveforms of the channel (measurement point) determined as noise, by interpolation calculation from signal waveforms around the channel thereof.

Figure 13:
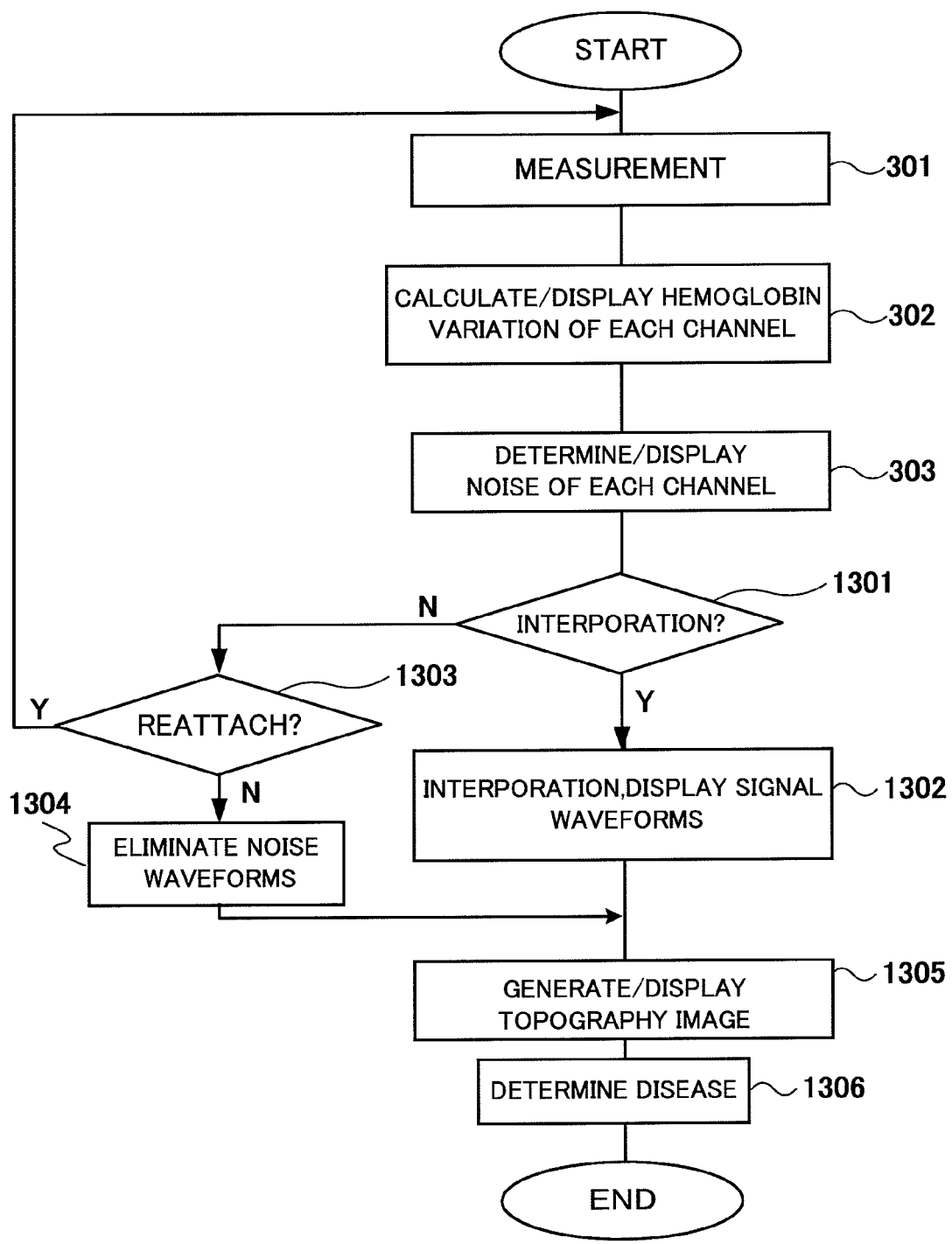
FIG. 13 is a flow chart showing an operation of the biological photometric device in the second embodiment of the present invention.

In step 303 of FIG. 13, noise detecting unit 34A generates a topography image after executing noise detection and display of the detection result in the same manner as the first embodiment, and performs display for asking the operator whether to generate the signal waveforms of the noise channel by interpolation calculation or not, before generating the topography and displaying it to display 50.

In the case the operator instructs execution of interpolation in response to the above-mentioned display, oxygenated hemoglobin variation or deoxygenated hemoglobin variation of the noise channel is generated by interpolation calculation using the surrounding normal signal waveforms. Then the signal waveforms obtained by interpolation calculation are displayed to the display position of the aforementioned channels by replacing the noise signal waveforms (step 1302).

Next, image generating unit 32 generates topography images using the hemoglobin variation signals of the normal channels and the hemoglobin variation signals generated by the interpolation calculation (step 1305), and disease-determining unit 35 determines disease using the hemoglobin variation signals of the normal channels and the hemoglobin variation signals generated by the interpolation calculation (step 1306).

On the other hand, in the case that the operator instructs using input unit 60 not to perform interpolation in step 1301, noise detecting unit 34 reattaches probe holder 226, improves contact condition of the end face of optical fibers 311~314 and 321~325 to object 17, and make a display for asking the operator whether to perform measurement again or not (step 1303).

In the case that the operator selected not to reattach the probe holder in response to the above-mentioned display, noise detecting 34 deletes the waveforms of the noise channel (step 1304), and image generating unit 32 and disease-determining unit 35 generates topography images using only the hemoglobin variation signals of the normal channels, and determines disease (step 1305). Here, the topography image is the image wherein the time variation is made into 2-dimensional distribution image, and the respective topographies can be selectively displayed, or simultaneously displayed on the same screen.

When the operator selected to execute the reattachment of probe holder 226 (including the improvement of the contact condition of optical fibers 311~314, 321~325 and the object) in response to the display in step 1303, the step returns to step 301, and the re-measurement is executed by the operator through the re-measurement operation inputted to input unit 60.

In this way, in the second embodiment, signal waveforms of the noise channels can be generated using interpolation calculation as being selected by the operator, and in the case of small noise which does not influence the image generation or disease determination very much, image generation and disease determination can be executed using interpolation calculation without re-starting the measurement.

While the present invention has been described in the above-mentioned first and second embodiments by citing embodiments that enable determination and detection of all the low S/N noise, mirror noise and spike noise, the present invention is capable of variably changing the embodiment so that at least one of low S/N noise and mirror noise can be determined and detected, and two or more of the first noise detecting means, the second noise detecting means and the third noise detecting means can be arbitrarily combined as need arises.

Also, in the case of eliminating the noise waveforms by performing noise determination using the signal waveforms within a predetermined time range, while the device is configured in the above-mentioned first and second embodiments to execute image generation and disease determination by eliminating the entire waveform of the channel thereof, the present invention is not limited to such configuration. It is possible for the present invention to variably set the device configuration to, for example, divide the entire measurement period into a plurality of time zones and perform noise determination on the respective zones, and when zones of the normal signals are detected, the signals of those zones can be used for image generation and disease determination without being eliminated.

Also, while it is configured in the above-mentioned embodiments that CPU is set in the calculation controller made to perform calculation, chart creation, image construction and determination in the respective units, a microprocessor may be set in the respective units instead.

The invention claimed is:

1. A biological photometric device comprising:
    a light irradiating unit for irradiating light having a predetermined wavelength and responding to oxygenated hemoglobin and deoxygenated hemoglobin, to an object to be examined via irradiating optical fibers;
    a light detecting unit for detecting and amplifying the light passed through the object via detecting optical fibers;
    a signal processing unit for calculating hemoglobin time variation information of oxygenated hemoglobin, deoxygenated hemoglobin and total hemoglobin in the body of the object from the signals detected by the light detecting unit, which has noise detecting means for determining and detecting from the time variation information at least one type of a noise attributed to the existence of obstructions to the passing of light between the object and end surface of the optical fibers, and the noise attributed to damage of the light irradiating unit; and
    a display unit for displaying the noise signals determined and detected by the signal processing unit, in a way capable of discriminating the type of noise.

2. The biological photometric device according to claim 1, wherein the signal processing unit comprises a first noise detecting means for determining and detecting noise attributed to the existence of obstructions to passing of light between the object and end surface of the optical fibers, and a second noise detecting means for determining and detecting noise attributed to damage of the light irradiating unit.

3. The biological photometric device according to claim 2, wherein the first noise detecting means calculates a standard deviation value with respect to time change of the detection signals, and determines the signals as noise signals when the obtained standard deviation value is more than a predetermined threshold value and when a gain in the light detecting unit is more than the predetermined threshold value.

4. The biological photometric device according to claim 2, wherein the second noise detecting means comprises:
    means for obtaining time correlation value r with respect to time variation information of the oxygenated hemoglobin and deoxygenated hemoglobin; and
    means for obtaining standard deviation values $SD_{oxy}$, $SD_{deoxy}$ and $SD_{total}$ with respect to time change information of the oxygenated hemoglobin, deoxygenated hemoglobin and total hemoglobin,
    characterized in that the second noise detecting means determines the signals as being noise signals when:

$r \leq r_0$;

$SD_{oxy} \geq S_2 \times SD_{total}$; and $SD_{deoxy} \geq S_3 \times SD_{total}$ ($r_0$, $S_2$ and $S_3$ are values set in advance).

5. The biological photometric device according to claim 2, wherein the signal processing unit has a third noise detecting means for determining and detecting noise attributed to gaps between optical fiber apertures and the object over a minute period of time caused by the relative positional displacement of the object and the optical fibers.

6. The biological photometric device according to claim 5, wherein the signal processing unit includes:
    means to convert time variation information of the oxygenated hemoglobin, deoxygenated hemoglobin and total hemoglobin into a time variation chart, and outputting it to a display unit; and means to impart the information to the time variation chart for enabling an operator to recognize the kind of noise.

7. The biological photometric device according to claim 6, wherein the information for making the kind of noise identifiable is the background color of the time variation chart.

8. The biological photometric device according to claim 6, wherein the information for making the kind of noise identifiable is texture information.

9. The biological photometric device according to claim 2, wherein the signal processing unit includes:
   means to convert time change information of the oxygenated hemoglobin, deoxygenated hemoglobin and total hemoglobin into a time change chart and output it to a display unit; and
   means to impart information to the time variation chart for enabling the operator to discriminate the kind of noise.

10. The biological photometric device according to claim 9, wherein the information for making the kind of noise identifiable is the background color of time variation chart.

11. The biological photometric device according to claim 9, wherein the information for making the kind of noise identifiable is textual information.

12. The biological photometric device according to claim 1, wherein:
   the light irradiating unit has a plurality of irradiating optical fibers for irradiating light to a plurality of points of the object;
   the light detecting unit has a plurality of detecting optical fibers for detecting light at a plurality of points on the body surface of the object that are respectively different from the plurality of points being irradiated by the irradiating optical fibers; and
   the signal processing unit calculates the time change information of the plurality of measurement points determined by the arrangement of the irradiating optical fibers and the detecting optical fibers, performs noise determination, displays the hemoglobin time change information with respect to the plurality of measurement points to a display screen of a display unit by disposing them to correspond to the position of the measurement points, and simultaneously displays discrimination data for indicating to the display region measurement points determined as being noise signals.

13. The biological photometric device according to claim 12, wherein the signal processing unit comprises means to construct a topography image using the hemoglobin time change information with respect to the plurality of measurement points, and to output the constructed topography image to a display unit.

14. The biological photometric device according to claim 13, wherein the signal processing unit is further configured to construct topography images using only normal signals by eliminating the hemoglobin time change information of the measure points, out of the plurality of measurement points, that are determined by the noise detecting unit as noise signals.

15. The biological photometric device according to claim 12, wherein the signal processing unit comprises means for calculating signals that are assumed to be normally measured with respect to the measurement points where noise signals are measured, by interpolation calculation using normal signals of the adjacent plurality of measurement points.

16. The biological photometric device according to claim 15, wherein the signal processing unit is further configured to construct topography images by replacing the hemoglobin time change information of the measure points out of the plurality of measure points that are determined by the noise detecting unit as noise signals, with signals obtained by the interpolation calculation means, and to output the constructed topography images to a display unit.

17. The biological photometric device according to claim 15, wherein the signal processing unit has a disease determining unit for performing disease determination using the hemoglobin time change information of the object, and the disease determining unit determines disease by replacing noise signals detected by the noise detecting unit with the signals obtained by the interpolation calculation means.

18. The biological photometric device according to claim 12, wherein the signal processing unit has a disease determining unit for performing disease detection using the hemoglobin time change information of the object, and the disease detecting unit eliminates the noise signals detected by the noise detecting unit and performs disease detection using only normal signals.

19. The biological photometric device according to claim 1 wherein the noise detecting unit is configured to cause the display unit to display a denotation for inducing re-measurement to the operator when noise signals are detected.

20. The biological photometric device according to claim 19, comprising an input unit for an operator to input operation commands, characterized in performing re-measurement when the command is inputted from the input unit to perform re-measurement with respect to the denotation for inducing the re-measurement.

* * * * *